United States Patent [19]
March et al.

[11] Patent Number: 5,171,217
[45] Date of Patent: Dec. 15, 1992

[54] METHOD FOR DELIVERY OF SMOOTH MUSCLE CELL INHIBITORS

[75] Inventors: Keith L. March, Carmel; David R. Hathaway; Robert L. Wilensky, both of Indianapolis, all of Ind.

[73] Assignee: Indiana University Foundation, Bloomington, Ind.

[21] Appl. No.: 662,194

[22] Filed: Feb. 28, 1991

[51] Int. Cl.$^5$ ............................................. A61M 31/00
[52] U.S. Cl. ...................................... 604/53; 604/269; 128/898
[58] Field of Search ................. 604/28, 48, 49, 51–53, 604/54, 55, 93, 265, 266, 269; 128/897, 898; 424/450

[56] References Cited

U.S. PATENT DOCUMENTS

| | | | |
|---|---|---|---|
| 4,531,936 | 7/1985 | Gordon | 604/49 |
| 4,637,815 | 1/1987 | Lemole | 604/28 |
| 4,820,732 | 4/1989 | Shell et al. | 514/573 |
| 4,824,436 | 4/1989 | Wolinsky | 604/53 |
| 4,839,175 | 6/1989 | Guo et al. | 424/450 |
| 4,955,878 | 9/1990 | See et al. | 604/181 |
| 4,989,601 | 2/1991 | Marchosky et al. | 604/51 |
| 5,049,132 | 9/1991 | Shaffer et al. | 604/96 |
| 5,059,178 | 10/1991 | Ya | 604/96 |
| 5,092,841 | 3/1992 | Spears | 604/96 |

FOREIGN PATENT DOCUMENTS 8912478 12/1989 World Int. Prop. O. .

OTHER PUBLICATIONS

Use of a Perforated Balloon Catheter to Deliver Concentrated Heparin into the Wall of the Normal Canine Artery, Wolinsky et al., J. Am. Coll. Cardiol., 15:475 (1990).

Local Anticoagulation Without Systemic Effect Using a Polymer Heparin Delivery System, Okada et al., Stroke 19:1470 (1988).

Effect of Controlled Adventitial Heparin Delivery on Smooth Muscle Cell Proliferation Following Endothelial Injury, Edelman, Proc. Natl. Acad. Sci. U.S.A. 87:3773 (1990).

Laser Balloon Angioplasty: Potential for Reduction of the Thrombogenicity of the Injured Arterial Wall and for Local Application of Bioprotective Materials, Spears et al., unpublished paper presented and copies distributed at the Fourth Annual International Workshop on the Future Direction of Interventional Cardiology, Sep. 7–8, 1990, Santa Barbara, Calif.

*Primary Examiner*—John D. Yasko
*Assistant Examiner*—Adam J. Cermak
*Attorney, Agent, or Firm*—Baker & Daniels

[57] ABSTRACT

A method and composition for delivering a drug to an affected intramural site for sustained release in conjunction with or following balloon catheter procedures, such as angioplasty. The drug, carried by microparticles of a physiologically-compatible, biodegradable polymer is injected under directed pressure into the wall of a body vessel in the region of the affected site.

13 Claims, No Drawings

METHOD FOR DELIVERY OF SMOOTH MUSCLE CELL INHIBITORS

BACKGROUND OF THE INVENTION

A number of clinical conditions have in common the prospect for successful treatment by balloon catheterization to restore useful configuration to internally distorted vessels. The most prominent application of this technique is in the treatment of coronary artery disease.

Percutaneous transluminal coronary angioplasty (PTCA) has been demonstrated to provide an effective alternative to coronary bypass surgery in relieving stenoses of atherosclerotic plaque within coronary arteries. In this procedure, an inflatable balloon at the distal end of a catheter is positioned in the region of a stenosis. The balloon is inflated under fluid pressure to reconfigure the narrowed lumen and permit increased blood flow through the affected artery. It is not unusual that inflation-deflation cycles will be repeated several times where the narrowing is severe. This mechanical violence to the arterial wall may produce the desired opening of the artery, but in delayed consequence the procedure is followed by a 30-50% incidence of restenosis at or near the injured site. No pharmacologic or mechanical intervention has proven effective in addressing this problem.

Studies have suggested a number of causes underlying restenosis. These studies have indicated that angioplasty may produce endothelial denudation, injury to the vascular wall and rupture of the vasa vasorum. The accompanying uncontrolled proliferation of smooth muscle cells within the arterial wall has been widely implicated as a prominent factor in the resulting restenosis.

Among approaches to dealing with such restenoses has been the delivery of smooth muscle cell growth regulators, such as heparin, to the artery wall at the site of actual or incipient restenosis following angioplasty. U.S. Pat. No. 4,824,436 (Wolinsky) describes a catheter and its use for pressurized local delivery of heparin in solution. Local delivery of heparin and penetration within the arterial wall has been demonstrated by Wolinsky, "Use of A Perforated Balloon Catheter To Deliver Concentrated Heparin Into The Wall Of The Normal Canine Artery," J. Am. Coll. Cardiol. 15:475 (Feb. 1990). However, such a method does not afford sufficient contact at the site of an angioplasty before the drug diffuses to ineffective concentrations.

To increase residence time and provide localized inhibiting activity of heparin in controlling smooth muscle cell proliferation, Edelman et al., "Effect Of Controlled Adventitial Heparin Delivery For Smooth Muscle Cell Proliferation Following Endothelial Surgery," Proc. Natl. Acad. Sci. 87:3773 (May 1990), have implanted heparin in a polymer matrix directly on the adventitia as a means for obtaining local and sustained release of the smooth muscle cell inhibitor. This approach does not lend itself to treating restenosis in humans since it involves a surgical procedure.

Adaptations of balloon catheters also may be used in such conditions as benign prostatic hypertrophy, malignant disorders of various tissues available to tubular access, occlusions in peripheral vasculature, clearing and restoring prostatic and other intrusions in the urethra, opening fallopian tubes and dilating esophageal structures. Such interventions frequently have in common the need for repetitive treatment. The problems that typically arise in practice or in concept are the difficulty of delivery and the provision of adequate residence time in the face of inevitable and premature loss of drug from the desired site through rapid diffusion or erosion.

It is therefore an object of this invention to provide method and compositions for delivering a drug for sustained release at a desired intramural site by injection into the access vessel.

Another object is to provide a method and compositions for delivering a drug to the desired intramural site in a biodegradable polymeric carrier.

A further object is to provide method and compositions for delivering a smooth muscle cell inhibitor for sustained release in the region of a restenosis following angioplasty.

SUMMARY OF THE INVENTION

Broadly, this invention is a method and composition for delivering a drug to an affected intramural site for sustained release. The drug, carried by microparticles of a physiologically-compatible, biodegradable polymer, is injected under directed pressure into the wall of a body vessel in the region of the affected site. By "body vessel" is meant a hollow viscus or access route through which drug delivery means, such as a catheter or other injection device, may inject drug-polymer microparticles.

In broad scope this invention is directed to application in conjunction with or following balloon catheter procedures for recanalization in such conditions as coronary artery disease, benign prostatic hypertrophy, malignant disorders of various tissues available to tubular access, occlusions in peripheral or cardiac vasculature, clearing and restoring prostatic and other intrusions in the urethra, opening fallopian tubes, and dilating esophageal structures. Tissue injury and attending proliferation of smooth muscle cells is often a contributing factor in complications from these procedures. When applied in coronary artery disease, this invention is useful in conjunction with any interventional process of the coronary artery, such angioplasty, atherectomy, laser recanalization (e.g., excimer laser), laser angioplasty and stent placement.

In preferred embodiment, this invention embraces a method and composition for treating restenosis immediately following procedures for vessel recanalization involving vascular injury, particularly angioplasty. A drug, such as heparin, carried by microparticles of a physiologically-compatible, biodegradable polymer, such as polylactide or a polyanhydride, is delivered for sustained release of drug at the affected intramural site by injection under directed pressure into the arterial wall in the region of incipient restenosis.

The drugs are released slowly, providing a residence time sufficient for treatment or control at the site of smooth muscle cell proliferation in the case of restenosis following angioplasty. The polymeric material degrades and diffuses inoffensively.

As contemplated herein, "treating" restenosis embraces application of the invention to incipient restenosis as well as established restenosis. For example, administration of a smooth muscle cell inhibitor may precede, attend or follow angioplasty (immediately or within about two weeks after the procedure).

DESCRIPTION OF THE INVENTION

Each condition within the scope of medical approach utilizing this invention has its own etiology and therapy. However, each may involve delivery to affected sites within vessel walls of a drug incorporated on or within a physiologically-compatible, biodegradable polymeric microparticle from which the drug is gradually released into the surrounding tissue substrate, thus affording the necessary drug residence time in the intramural environment to be treated. The residence time can be adjusted by means known to the art of designing controlled release combinations of drug and microparticulate carrier.

For example, this invention provides advantageous therapy to inhibit or treat restenosis following angioplasty in atherosclerotic coronary arteries. A smooth muscle cell-inhibiting drug is delivered by transcatheter intramural injection in the arterial region of a restenosis that has been or is immediately to be reconfigured by angioplasty. The drug is contained within microparticles of a physiologically compatible, biodegradable polymer from which it is slowly released to control smooth muscle cell proliferation and inhibit or treat restenosis. The drugs are those recognized in the art as useful in controlling smooth muscle cell proliferation in vitro or in vivo. as hereinafter described.

Smooth muscle cell proliferation is a common, though not exclusive, etiological phenomenon of these conditions. Treatment of choice may be selected from a broad variety of drugs known to inhibit smooth muscle cell proliferation, including:

A. Agents that modulate intracellular $Ca^{2+}$ or $Ca^{2+}$-binding proteins
   a) L-type $Ca^{2+}$ channel blockers (e.g., nifedipine, diltiazem, verapamil)
   b) T-type $Ca^{2+}$ channel blockers (e.g., amiloride)
   c) calmodulin antagonists (e.g., $H_7$)
   d) inhibitors of the sodium/calcium antiporter (e.g., amiloride)
   e) inhibitors of the ryanodine receptor (e.g., ryanodine)
   f) inhibitors of the $IP_3$ receptor (e.g., heparin)
B. Receptor blockers for contractile agonists (e.g., α-adrenergic blocking agents, angiotensin II receptor antagonists and receptor antagonists for histamine, serotonin, endothelin)
C. Inhibitors of the sodium/hydrogen antiporter (e.g., amiloride and its derivatives)
D. Protease inhibitors (e.g., serine protease, metalloendoproteases and aspartyl protease and thiol protease inhibitors (e.g., benzyloxycarbonyl-leu-norleucinal (calpeptin) and acetyl-leu-leu-norleucinal)
E. Nitrovasodilators (e.g., isosorbide dinitrate)
F. Phosphodiesterase inhibitors (e.g., isobutyl methylxanthine)
G. Phenothiazines (e.g., amytriptyline)
H. Growth factor receptor antagonists (for platelet-derived growth factor (PDGF), epidermal growth factor, interleukins, transforming growth factors alpha and beta, and acidic or basic fibroblast growth factors)
I. Anti-mitotic agents (e.g., colchicine, anthracyclines and other antibiotics, folate antagonists and other anti-metabolites, vinca alkaloids, nitrosoureas, DNA alkylating agents, purine antagonists and analogs, pyrimidine antagonists and analogs, alkyl sulfonates)
J. Immunosuppressive agents (e.g., adrenocorticosteroids, cyclosporine)
K. Antisense oligonucleotides (e.g., sequences complementary to portions of mRNA encoding DPGF or other growth factors)
L. Protein kinase inhibitors (for tyrosine kinases, protein kinase C, myosin light chain kinase, $Ca^{2+}$/calmodulin kinase II, casein kinase II).

The size of microparticles carrying such drugs is determined and limited primarily by considerations of thrombus formation, plugging of downstream capillaries and effective discharge of microparticles from the catheter. Although other factors, such as varying densities of the arterial layers and associated plaque, will to some degree affect distribution of particle deposits, the gross effect should not materially alter beneficial results of therapy. This is because diffusion of drug from the microparticles affords sufficient intramural penetration to offset variations in local microparticle accumulations.

The drug-polymer combinations in which the polymer is physiologically-compatible and biodegradable can be prepared by methods known in the art. In these drug-carriers the drugs are linked by occlusion in matrices of the polymer, bound for release by hydrolysis or chemical action involving covalent linkages, encapsulated in polymeric microcapsules or by other means of releasable attachment.

Polymers especially suited to the drug-polymer combinations of this invention have molecular weights in the range of about 10,000 to 2,000,000, the range of about 50,000 to 500,000 being preferred. The weight ratio of active ingredient to polymer may be from about 1:50 to 1:1. A drug content of about 15 to 25% is preferred. Microparticles range in size from about 0.5 to about 25 microns, a range of about 5 to 7 microns being preferred.

Examples of biodegradable polymers incorporating drugs for sustained release include poly-1-lactide, poly-dl-lactide, polyglycolide, poly(glycolide-co-dl-lactide), polyanhydrides, polyorthoesters, poly(α-hydroxybutyric acid), poly-p-dioxinone and block polymers of polyglycolide, trimethylene carbonate and polyethylene oxide. Preparation of microparticles of such polymers containing drugs are exemplified in European Patent Application 0,374,531 (Brizzolara et al.). This application describes preparation of microcapsules by phase separation, interfacial reactions, physical methods and solvent evaporation methods.

Other microparticles are described in European Patent Application 0,374,532, in which microencapsulation by phase separation is conducted. This process involves dispersion of the milled solid active ingredient of desired particle size in a solution of a polymer, addition of a phase inducer to cause the polymer to separate (or coacervate) as solvent-polymer droplets to which the drug adheres, and addition of a hardening solvent to extract the polymer solvent to yield solid microparticles, which are recovered by filtration and then dried. The patent describes details of the process and represents an example of teachings in the art of the preparation of drug-polymer combinations suited to the present invention.

Description of additional microparticle compositions are to be found in European Patent Application 0,251,476 (Eppstein and Schryver), in which are described additional techniques of coacervation that may be used to prepare suitable drug-polymer microparticles, particularly polylactide and poly(lactide-co-glycolide) polymers and copolymers. Other microparticles may be prepared as described in U.S. Pat. No. 3,773,919 and European Patent Application 0,052,510.

In addition to synthetic polymers, natural products such as proteins, including albumin, and other amino acid polymers and polysaccharides afford microparticle carriers giving sustained release of incorporated drugs. These are exemplified in U.S. Pat. No. 4,352,883 (Lim) and U.S. Pat. No. 3,464,413 (Goldfarb et al.). Of particular interest are the techniques described in U.S. Pat. No. 4,898,734 (Mathiowitz et al.) in which spheres are formed by interfacial polymerization, hot melt microencapsulation, solvent removal, solvent evaporation and other methods further described by Mathiowitz et al. in "Photochemical Rupture Of Microcapsules: A Model System," J. App. polym. Sci. 26:809 (1981).

An example of a natural polymer-drug combination is described in "Phagocytosis of Microspheres Containing an Anticancer Agent by Tumor Cells In Vitro," Kramer and Burnstein, Life Sciences, 19:515–520 (1976). In this method, a 25% human serum albumin solution containing drug is emulsified in cottonseed oil and heat-denatured at 175° C. to produce microspheres. The spheres are washed with ether and water, suspended by sonication in culture medium at pH 7.1 using 0.1% Tween 80 as a suspending agent. The spheres are used immediately. These methods are suitable for water soluble drugs which are stable up to 200° C.

An example of preparation of a drug-polylactic acid combination is described in "New Long-Acting Injectable Microcapsule Contraceptive System," Beck et al., Am. J. Obstet. Gynecol., 135:419 (1979). The polymer d,l-polylactic acid (molecular weight 90,000), is dissolved in a mixed solvent of chloroform and acetone. The resulting solution is chilled to about 6° C. The micronized drug is added to the chilled solution and the mixture stirred vigorously to give a uniform suspension. The suspension is dispersed by stirring at about 300 r.p.m. in a cold (about 6° C.) aqueous solution of 5% by weight of polyvinyl alcohol. The pressure in the reaction vessel is reduced to about 500 mm. The resulting product is stirred at about 300 r.p.m. at about 6° C. for approximately 10 hours. The temperature is then allowed to rise to room temperature. The microspheres encapsulating the drug are formed as the acetone and chloroform evaporates. After approximately 16 hours the vacuum is released. The microcapsules are isolated by filtration, washed with deionized water and allowed to dry.

Another method is described in "Controlled Release of a Luteinizing Hormone-Releasing Hormone Analogue from Poly(d,l-lactide-co-glycolide) Microspheres," Sanders et al. in J. Pharm. Sci., 73:1294 (1984). An aqueous solution of drug and a solution of poly(d,l-lactide-co-glycolide) in dichloromethane were coemulsified to form a water-in-oil emulsion. A nonsolvent for the copolymer is then added to precipitate out the polymer. The suspension of microspheres is added to a large volume of nonsolvent to complete the extraction of dichloromethane and harden the microspheres. The microspheres are then washed and dried.

The drug may be covalently bonded to a biodegradable polymer, as described Freijen et al., J. Pharm. Sci., 69:871 (1980). The drug is derivatized to contain an acid chloride functional group. Drugs with an alcohol, carboxylic acid, ester or other functional group are converted to an acid chloride by known methods. The polymers used are poly(hydroxyalkyl)-L-glutamines, which are dissolved in a mixture of anhydrous dimethylformate and pyridine. The dissolved polymer is then reacted with the derivatized drug. The drug-bound polymer is isolated by repeated precipitation in ethylacetate. Excess polymer may be required to maximize the amount of polymer bound drug produced and to speed up the reaction.

Suitable catheters are those designed to provide a chamber to minimize downstream escape of microparticles under the pressures required for arterial (or other organ) wall penetration. Conventional catheters can be modified for lateral discharge into the arterial wall. U.S. Pat. Nos. 4,824,436 (Wolinsky), 4,423,725 (Baran et al.) and 3,173,418 (Baran et al.) illustrate catheters suitable for use with this invention. Whatever specific design is chosen, pressures in the range of about 2 to about 10 atm. assure adequate penetration consistent with containing the discharge against undue downstream escape. A preferred range of pressures is about 3 to about 6 atm.

Delivery of these microparticles containing therapeutic agents can be via a catheter in a conscious patient without the need for general anesthesia and surgical implantation. For the first time, deposition of such agents is possible in all layers of, for example, the blood vessel or other affected vessel tissue.

Since the microparticles are not in direct contact with the blood, the likelihood of thrombosis is greatly reduced. Because the microparticles are of minute size, distal embolization is unlikely to cause serious restriction of blood flow in the affected artery.

The microparticles are biodegradable. Their use therefore avoids the necessity of leaving foreign substances in the body for an extended period with attendant possible complications. Moreover, it is not necessary to heat or otherwise process the microparticle after extrusion from the catheter because, once deposited, the drugs will diffuse slowly without further manipulation.

The feasibility of injecting suitable polymeric carriers into an access vessel as a means for delivering a carrier-drug combination depends on the carrier reaching the desired intramural site. This was demonstrated by first inducing in rabbits a focal atherosclerotic lesion and restenosis by producing endothelial injury through air desiccation and adoption of a high cholesterol diet (2% cholesterol, 6% peanut oil). Angioplasty was performed at the site of the induced focal lesions. Duration of cholesterol feeding prior to angioplasty was three weeks. The angioplasty balloon used to induce restenosis was 0.25 mm larger than the proximal, normal arterial segment. The duration of time between angioplasty and sacrifice of the test animals was randomized to evaluate the retention of microparticles over this time. Totally occluded arteries were included only if they opened successfully on balloon angioplasty.

Polystyrene particles (Seradyn, Indianapolis) having an average diameter of 5 μm (coefficient of variation 3%) were suspended in sterile saline solution to a final concentration of approximately $6 \times 10^6$ microparticles per milliliter. At this concentration the microparticles did not form aggregates. About 10 ml of solution was drawn into a standard angioplasty inflation device. A porous infusion catheter (USCI Division of Bard, Inc.) was primed according to the manufacturer's specifications. The catheter was placed in the artery in the exact area of prior balloon dilatation. Injection pressure was randomized, with one artery injected at 5 atmospheres and the contralateral artery at 3 atmospheres. The microparticle suspension was injected for 45 seconds and the administered volume noted. The catheter was removed and a final radiograph obtained.

Animals were sacrificed following angioplasty and infusion immediately, and after one, three, seven and fourteen days. During the period prior to sacrifice, the animals were placed on a regular diet. Sacrifice and arterial perfusion fixation methods were those described by Sarembock et al., "Influence Of Inflation Pressure And Balloon Size On The Development Of Intimal Hyperplasia After Balloon Angioplasty," Circulation 80:1029 (1989). The arteries were dissected from overlying tissue, cut into cross-sections of 3-4 mm, and the distal end of each segment was marked for orientation. The segments were embedded in paraffin, sectioned and stained. Arterial cross-sections were evaluated for location, quantity and depth of penetration of microparticles within the vessel wall. The microparticles were counted using a 250× magnification in a Zeiss inverted stage microscope. The image was processed and analyzed by computer and by a morphometric and densitometric image processing and analysis system (Analytical Imaging Concepts).

Nineteen animals underwent intramural injection of microparticles. Total unilateral arterial occlusions could not be opened in four animals, so a total of 34 arteries were injected. Fifteen arteries underwent injection at 3 atmospheres. In 28 of the corresponding 73 arterial sections, microparticles were observed (30%).

Nineteen arteries underwent injection at 5 atmospheres. Forty-seven of the 99 sections (47%) exhibited microparticles.

Of the 34 arteries, 30 showed microparticle deposition in one or more histologic sections. Twenty-one exhibited microparticles in the neointima, 12 in the media and 25 in the adventitia. The distribution of microparticles deposited in the layers of the arterial wall is shown in Table I. It appeared that injection pressure did not substantially affect the radial distribution of microparticles into arterial layers, as shown in Table II. Prominent radial asymmetry was generally noted in the distribution of microparticles. No distinct microparticle pathway was observed.

The study shows that microparticles injected with an infusion catheter following balloon angioplasty are retained for at least two weeks in the neointimal, medial and adventitial layers of the arterial wall. This demonstrates the feasibility of intramural injection of microparticles to carry drugs to an affected site.

In the work described, the animal model was pretreated to provide a representative condition of an artery wall containing atherosclerotic plaque. Microparticles, injected at reasonable pressures, penetrated to all depths of the wall, a result important to the success of treatment of intramural processes occurring at a variety of levels within the wall, such as smooth muscle cell proliferation implicated in the process of restenosis.

This showing of long-term in vivo retention of microparticulate matter following intra-arterial wall deposition via a catheter produced results contrasting favorably with earlier studies showing that fluoresceinated heparin remained in a canine arterial wall for only 72 hours. Such short-term deposition is not believed sufficient to prevent smooth muscle proliferation and consequent restenosis.

TABLE I

NUMBER OF ARTERIES WITH MICROPARTICLE DEPOSITION AND THE LOCATION OF MICROPARTICLES WITHIN THE ARTERIAL WALL IN RELATIONSHIP TO INJECTION PRESSURE AND TIME INTERVAL FOLLOWING INJECTION.

| Time | n = | Neointima | 5 ATM Media | Adventitia | n = | Neointima | 3 ATM Media | Adventitia |
|---|---|---|---|---|---|---|---|---|
| Immediate | 4 | 2 | 2 | 4 | 3 | 2 | 1 | 2 |
| 1 Day | 4 | 3 | 2 | 3 | 3 | 3 | 0 | 2 |
| 3 Days | 4 | 3 | 0 | 1 | 4 | 2 | 1 | 3 |
| 7 Days | 3 | 3 | 2 | 2 | 2 | 0 | 0 | 2 |
| 14 Days | 4 | 3 | 3 | 3 | 3 | 0 | 1 | 3 |
| Total | 19 | 14 | 9 | 13 | 15 | 7 | 3 | 12 |

TABLE II

Average number of microparticles deposited per arterial section when microparticles were observed.

| Injection Pressure | Neointima | Media | Adventitia |
|---|---|---|---|
| 5 ATM | 302 ± 1139<br>n = 23 | 1411 ± 100<br>n = 15 | 1411 ± 5882<br>n = 30 |
| 3 ATM | 31 ± 79<br>n = 10 | 2 ± 2<br>n = 6 | 268 ± 835<br>n = 22 | n = number of arterial segments exhibiting microparticles
Differences between injection pressure were not statistically significant.

We claim:

1. A method for delivering a drug to an affected intramural site for sustained release comprising:
    injecting a smooth muscle cell inhibitor under directed pressure into the wall of a body vessel in the region of the affected intramural site, said drug being carried by microparticles of a physiologically-compatible, biodegradable polymer.

2. The method of claim 1 in which the smooth muscle cell inhibitor is selected from the group of:
    A. Agents that modulate intracellular $Ca^{2+}$ or $Ca^{2+}$-binding proteins
    B. Receptor blockers for contractile agonists
    C. Inhibitors of the sodium/hydrogen antiporter
    D. Protease inhibitors
    E. Nitrovasodilators
    F. Phosphodiesterase inhibitors
    G. Phenothiazines
    H. Growth factor receptor antagonists
    I. Anti-mitotic agents
    J. Immunosuppressive agents
    K. Antisense oligonucleotides and
    L. Protein kinase inhibitors,
    and the polymer is selected from the group of biodegradable polylactic acid, polyglycolic acid and polyanhydride-base polymers.

3. The method of claim 2 in which the smooth muscle cell inhibitor is selected from the group of:
    A. Agents that modulate intracellular $Ca^{2+}$ or $Ca^{2+}$-binding proteins, said agents being selected from the group of
        a) L-type $Ca^{2+}$ channel blockers,
        b) T-type $Ca^{2+}$ channel blockers, c) calmodulin antagonists,
d) inhibitors of the sodium/calcium antiporter,
e) inhibitors of the ryanodine receptor, and
f) inhibitors of the IP$_3$ receptor;
B. Receptor blockers for contractile agonists, in which the receptor blockers are selected from the group of α-adrenergic blocking agents, angiotensin II receptor antagonists and receptor antagonists for histamine, serotonin and endothelin;
C. Inhibitors of the sodium/hydrogen antiporter, in which the inhibitors are selected from the group of amiloride and its derivatives;
D. Inhibitors of protease, serine protease, metalloendoproteases and aspartyl protease, and thiol protease inhibitors selected from the group of benzyloxycarbonyl-leu-norleucinal (calpeptin) and acetyl-leu-leu-norleucinal;
E. Nitrovasodilators, wherein the nitrovasodilator is isosorbide dinitrate;
F. Phosphodiesterase inhibitors, wherein the phosphodiesterase inhibitor is isobutyl methylxanthine;
G. Phenothiazines, wherein the phenothiazine is amytriptyline;
H. Growth factor receptor antagonists for platelet-derived growth factor (PDGF), epidermal growth factor, interleukins, transforming growth factors alpha and beta, and acidic or basic fibroblast growth factors;
I. Anti-mitotic agents selected from the group of colchicine, anthracyclines and other antibiotics, folate antagonists and other anti-metabolites, vinca alkaloids, nitrosoureas, DNA alkylating agents, purine antagonists and analogs, pyrimidine antagonists and analogs, and alkyl sulfonates;
J. Immunosuppressive agents selected from the group of adrenocorticosteroids and cyclosporine;
K. Antisense oligonucleotides including sequences complementary to portions of PDGF or other growth factors;
L. Protein kinase inhibitors for tyrosine kinases, protein kinase C, myosin light chain kinase, Ca$^{2+}$/calmodulin kinase II and casein kinase II;
and the polymer is selected from the group of biodegradable polylactic acid, polyglycolic acid and polyanhydride-base polymers.

4. A method for preventing restenosis following a procedure for vessel recanalization involving vascular injury comprising: injecting a smooth muscle cell inhibitor for sustained release at the affected intramural site, said smooth muscle cell inhibitor being carried by microparticles of a physiologically-compatible, biodegradable polymer.

5. The method of claim 4 in which the smooth muscle cell inhibitor is selected from the group of:
A. Agents that modulate intracellular Ca$^{2+}$ or Ca$^{2+}$-binding proteins
B. Receptor blockers for contractile agonists
C. Inhibitors of the sodium/hydrogen antiporter
D. Protease inhibitors
E. Nitrovasodilators
F. Phosphodiesterase inhibitors
G. Phenothiazines
H. Growth factor receptor antagonists
I. Anti-mitotic agents
J. Immunosuppressive agents
K. Antisense oligonucleotides, and
L. Protein Kinase inhibitors and the polymer is selected from the group of biodegradable polylactic acid, polyglycolic acid and polyanhydride-base polymers.

6. The method of claim 5 in which the drug is selected from the group of
A. Agents that modulate intracellular Ca$^{2+}$ or Ca$^{2+}$-binding proteins, said agents being selected from the group of
a) L-type Ca$^{2+}$ channel blockers,
b) T-type Ca$^{2+}$ channel blockers,
c) calmodulin antagonists,
d) inhibitors of the sodium/calcium antiporter,
e) inhibitors of the ryanodine receptor, and
f) inhibitors of the IP$_3$ receptor;
B. Receptor blockers for contractile agonists, in which the receptor blockers are selected from the group of α-adrenergic blocking agents, angiotensin II receptor antagonists and receptor antagonists for histamine, serotonin and endothelin;
C. Inhibitors of the sodium/hydrogen antiporter, in which the inhibitors are selected from the group of amiloride and its derivatives;
D. Inhibitors of protease, serine protease, metalloendoproteases and aspartyl protease, and thiol protease inhibitors selected from the group of benzyloxycarbonyl-leu-norleucinal (calpeptin) and acetyl-leu-leu-norleucinal;
E. Nitrovasodilators, wherein the nitrovasodilator is isosorbide dinitrate;
E. Phosphodiesterase inhibitors, wherein the phosphodiesterase inhibitor is isobutyl methylxanthine;
G. Phenothiazines, wherein the phenothiazine is amytriptyline;
H. Growth factor receptor antagonists for platelet-derived growth factor (PDGF), epidermal growth factor, interleukins, transforming growth factors alpha and beta, and acidic or basic fibroblast growth factors;
I. Anti-mitotic agents selected from the group of colchicine, anthracyclines and other antibiotics, folate antagonists and other anti-metabolites, vinca alkaloids, nitrosoureas, DNA alkylating agents, purine antagonists and analogs, pyrimidine antagonists and analogs, and alkyl sulfonates;
J. Immunosuppressive agents selected from the group of adrenocorticosteroids and cyclosporine;
K. Antisense oligonucleotides including sequences complementary to portions of PDGF or other growth factors;
L. Protein kinase inhibitors for tyrosine kinases, protein kinase C, myosin light chain kinase, Ca$^{2+}$/calmodulin kinase II and casein kinase II;
and the polymer is selected from the group of biodegradable polylactic acid, polyglycolic acid and polyanhydride-base polymers.

7. The method of claim 6 in which the smooth muscle cell inhibitor is selected form the group of anti-mitotic agents, protease inhibitors and antisense oligonucleotides.

8. The method of claim 7 in which the smooth muscle cell inhibitor is colchicine and biodegradable polymer is a copolymer of lactic acid and glycolic acid.

9. The method for preventing restenosis of a coronary artery recanalized by angioplasty comprising: injecting a smooth muscle cell inhibitor for sustained release at the affected intramural site, said smooth muscle cell inhibitor being carried by microparticles of a physiologically-compatible, biodegradable polymer, said smooth muscle cell inhibitor being selected from the group of:
- A. Agents that modulate intracellular $Ca^{2+}$ or $Ca^{2+}$-binding proteins
- B. Receptor blockers for contractile agonists
- C. Inhibitors of the sodium/hydrogen antiporter
- D. Protease inhibitors
- E. Nitrovasodilators
- F. Phosphodiesterase inhibitors
- G. Phenothiazines
- H. Growth factor receptor antagonists
- I. Anti-mitotic agents
- J. Immunosuppressive agents
- K. Antisense oligonucleotides and
- L. Protein kinase inhibitors, and the polymer is selected from the group of biodegradable polylactic acid, polyglycolic acid and polyanhydride-base polymers.

10. The method of claim 9 in which the smooth muscle cell inhibitor is selected from the group of:
- A. agents that modulate intracellular $Ca^{2+}$ or $Ca^{2+}$-binding proteins, said agents being selected from the group of
  - a) L-type $Ca^{2+}$ channel blockers,
  - b) T-type $Ca^{2+}$ channel blockers,
  - c) calmodulin antagonists,
  - d) inhibitors of the sodium/calcium antiporter,
  - e) inhibitors of the ryanodine receptor, and
  - f) inhibitors of the $IP_3$ receptor;
- B. Receptor blockers for contractile agonists, in which the receptor blockers are selected from the group of α-adrenergic blocking agents, angiotensin II receptor antagonists and receptor antagonists for histamine, serotonin and endothelin;
- C. Inhibitors of the sodium/hydrogen antiporter, in which the inhibitors are selected from the group of amiloride and its derivatives;
- D. Inhibitors of protease, serine protease, metalloendoproteases and aspartyl protease, and thiol protease inhibitors selected from the group of benzyloxycarbonyl-leu-norleucinal (calpeptin) and acetyl-leu-leu-norleucinal;
- E. Nitrovasodilators, wherein the nitrovasodilator is isosorbide dinitrate;
- F. Phosphodiesterase inhibitors, wherein the phosphodiesterase inhibitor is isobutyl methylxanthine;
- g. Phenothiazines, wherein the phenothiazine is amytriptyline;
- H. Growth factor receptor antagonists for platelet-derived growth factor (PDGF), epidermal growth factor, interleukins, transforming growth factors alpha and beta, and acidic or basic fibroblast growth factors;
- I. Anti-mitotic agents selected from the group of colchicine, anthracyclines and other antibiotics, folate antagonists and other anti-metabolites, vinca alkaloids, nitrosoureas, DNA alkylating agents, purine antagonists and analogs, pyrimidine antagonists and analogs, and alkyl sulfonates;
- J. Immunosuppressive agents selected from the group of adrenocorticosteroids and cyclosporine;
- K. Antisense oligonucleotides including sequences complementary to portions of PDGF or other growth factors;
- L. Protein kinase inhibitors for tyrosine kinases, protein kinase C, myosin light chain kinase, $Ca^{2+}$/calmodulin kinase II and casein kinase II;

and the polymer is selected from the group of biodegradable polylactic acid, polyglycolic acid and polyanhydride-base polymers.

11. The method for preventing restenosis of a coronary artery recanalized by angioplasty comprising: injecting a smooth muscle cell inhibitor selected from the group of anti-mitotic agents, protease inhibitors and antisense oligonucleotides into the arterial wall in the region of angioplasty for sustained release, said smooth muscle inhibitor being carried by microparticles of a biodegradable polymer selected from the group of polylactic acid, polyglycolic acid and polyanhydride-base polymers and copolymers.

12. The method of claim 11 in which the anti-mitotic agent is colchicine.

13. The method of claim 12 in which the polymer is a copolymer of lactic acid and glycolic acid.

* * * * *